United States Patent [19]
Burbaum et al.

[11] Patent Number: 5,424,454
[45] Date of Patent: Jun. 13, 1995

[54] PROCESS FOR THE STEREOSELECTIVE PREPARATION OF L-ALANYL-L-PROLINE

[75] Inventors: Beverly W. Burbaum, Westfield; Chunshi Li, Hoboken; George W. Matcham, Bridgewater, all of N.J.

[73] Assignee: Celgene Corporation, Warren, N.J.

[21] Appl. No.: 249,326

[22] Filed: May 26, 1994

Related U.S. Application Data

[63] Continuation-in-part of Ser. No. 63,434, May 18, 1993, Pat. No. 5,319,098.

[51] Int. Cl.⁶ .......................................... C07D 207/12
[52] U.S. Cl. .................................................. 548/533
[58] Field of Search ........................................ 548/533

[56] References Cited

U.S. PATENT DOCUMENTS 5,319,098  6/1994  Burbaum et al. ................... 548/533

FOREIGN PATENT DOCUMENTS

0523449A2  1/1993  European Pat. Off. .

OTHER PUBLICATIONS

Blacklock et al., "Synthesis of Semisynthetic Dipeptides Using N-Carboxyanhydrides and Chiral Induction on Raney Nickel. A Method Practical for Large Scale", *J. Organic Chem.*, 53, pp. 836–844 (1988).

"Imidapril Hydrochloride", *Drugs of the Future*, Prous Science, 17(7), pp. 551–558 (1992).

Kleeman et al., *Pharmazeutische Wirkstoffe*, pp. 1154–1155 (1987).

Mukaiyama et al., "A Novel Method for the Preparation of Optically Active Dipeptide. Chemo- and Stereoselective Reduction of 2-Hydroxyimino Amides with Samarium Diiodide", *Chemistry Letters*, pp. 181–184 (1992).

Primary Examiner—Joseph Paul Brust
Attorney, Agent, or Firm—Mathews, Woodbridge & Collins

[57] ABSTRACT

L-alanyl-L-proline is stereoselectively prepared catalytically hydrogenating an N-(2-iminopropionyl)-L-proline in the presence of a metal hydrogenolysis catalyst and at a pH of less than about 4. Also disclosed are improved processes for production of N-pyruvyl-L-proline in which L-proline and a 2,2-disubstituted propionyl halide are allowed to react at a pH of at least 9 to produce an L-proline intermediate which is hydrolyzed at a pH range of from about 6.5 to about 8.5 to yield N-pyruvyl-L-proline.

5 Claims, No Drawings

PROCESS FOR THE STEREOSELECTIVE PREPARATION OF L-ALANYL-L-PROLINE

CROSS REFERENCE TO RELATED APPLICATION

This is a continuation-in-part of Ser. No. 08/063,434 filed May 18, 1993, now U.S. Pat. No. 5,319,098, the disclosure of which is incorporated herein by reference.

BACKGROUND OF THE INVENTION

The dipeptide L-alanyl-L-proline is a known chemical intermediate useful in the preparation of various pharmaceutical agents having enzyme inhibiting properties. Angiotensin converting enzyme for example is a carboxyl terminal dipeptidyl exopeptidase [E.C. 3.4.15.1] which converts angiotensin I into angiotensin II, a potent vasoconstrictor. Numerous compounds have been described which reduce blood pressure in humans by inhibiting the renin-angiotensin system (generally referred to as angiotensin converting enzyme inhibitors or simply ACE inhibitors).

Many of these synthetic ACE inhibitors have a dipeptide or tripeptide-type structure, typically but not invariably including an alanine component bound through its carboxy group to a nitrogen containing heterocyclic group in which a carboxy group is in the α-position to the nitrogen atom of the heterocyclic group. Two examples of such compounds are enalapril, which is $N^2$-[(S)-1-ethoxycarbonyl-3-phenyl-propyl]-L-alanyl-L-proline, and enalaprilat, which is $N^2$-[(S)-1-carboxy-3-phenylpropyl]-L-alanyl-L-proline.

In one reported synthesis of enalapril, L-alanyl-L-proline is coupled with an alkyl ester of 2-oxo-4-phenylbutyrate; see Blacklock et al., *J. Org. Chem.* 53, 836–841 (1988). L-alanyl-L-proline contains two chiral centers and a third chiral center is generated in this condensation. Although the condensation is reported to provide high diastereoselectivity, the ratio of the desired SSS diastereoisomer to the unwanted RSS diastereoisomer is reported to be 87:13.

The classical dipeptide synthesis in which the two amino acids in the form of protected derivatives are coupled and the two protecting groups are then removed also has been used in the preparation of L-alanyl-L-proline. For example, N-(t-butoxycarbonyl)-L-alanine can be coupled with the benzyl ester of L-proline in the presence of dicyclohexylcarbodiimide and the resulting benzyl ester of N-(t-butoxycarbonyl)-L-alanyl-L-proline treated with trifluoroacetic acid to remove the N-(t-butoxycarbonyl) group. Hydrolysis to cleave the benzyl ester then yields L-alanyl-L-proline. See Kleemann et al., *Pharmazeutische Wirkstoffe*, 1154 (1987).

Blacklock et al., supra, describe the preparation of L-alanyl-L-proline through the reaction of the unprotected proline (as the potassium salt) with a cyclic L-alanine N-carboxyanhydride, a 2,6-dioxo-4-substituted oxazolidine formed by the reaction of L-alanine and phosgene. While this so-called NCA chemistry offers many advantages, it requires the use of phosgene and careful control of the reactants during the course of the reaction.

Mukaiyama et al., *Chemistry Letters*, 1992, pages 181–184, describe the stereoselective preparation of various dipeptides through the reduction of 2-hydroxyimino amides with the lanthanide samarium diiodide.

DETAILED DESCRIPTION

The present invention pertains to a new process for the stereoselective preparation of L-alanyl-L-proline from inexpensive starting materials. In particular, the process involves the hydrogenation, in the presence of a metal hydrogenolysis catalyst and at a pH of less than about 4, of an imine (including hydroxyimine) of the formula:

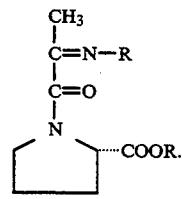

where R is a hydrogenolytically labile group and $R^1$ is hydrogen or a hydrogenolytically removable carboxy protecting group.

The hydrogenolytically removable carboxy protecting groups encompassed by $R^1$ typically are ester groups which are removable under sufficiently mild conditions of hydrogenation. This can be for example a lower alkyl ester of 1 to 12 carbon atoms such as methyl or ethyl or such an alkyl group which is (i) unsaturated such as vinyl or aryl, (ii) branched such as t-butyl, or (iii) substituted in the 1- or 2-position with lower alkoxy, such as for example, methoxymethyl, 1-methoxyethyl, and ethoxymethyl, lower alkylthio, such as for example methylthiomethyl and 1-ethylthioethyl; halogen, such as 2,2,2-trichloroethyl, 2-bromoethyl, and 2-iodoethoxycarbonyl; one or two phenyl groups each of which can be unsubstituted or mono-, di- or tri-substituted with, for example lower alkyl such as tert.-butyl, lower alkoxy such as methoxy, hydroxy, halo such as chloro, and nitro, such as for example, benzyl, 4-nitrobenzyl, diphenylmethyl, di-(4-methoxyphenyl)methyl; or aroyl, such as phenacyl.

While the process can be practiced with compounds of Formula I in which $R^1$ is such a hydrogenolytically removable carboxy protecting group, it is particularly advantageous that in the present process, the carboxy group in the proline portion of the molecule need not be protected; i.e., $R^1$ can be hydrogen, thereby reducing the number of synthetic steps by eliminating the need to remove such a protecting group.

The hydrogenolytically labile groups encompassed by R are described in, for example, Brieger, et al., Chem. Rev. 74, 567 (1974); Johnstone, et al., *Chem. Rev.* 85, 129 (1985); Augustine, "*Catalytic Hydrogenation: Techniques and Applications in Organic Synthesis*", Marcel Dekker, Inc, New York 1965; Rylander, , "*Catalytic Hydrogenation in Organic Synthesis*", Academic Press, Inc., New York, 1979; and Sinfelt, Catal. Lett., 9(3–4), 159–171 (1991), the contents of which are incorporated herein by reference. Such groups include cyano, allylic groups (including cyclic allylic groups such as cyclohex-2-en-1-yl), nitro, amino, alkoxy of 1 to 4 carbon atoms, hydroxy, carboxy, carbalkoxy, aryl such as phenyl and naphthyl, and aralkyl such as benzyl, phenethyl and similar groups as discussed above in greater detail in connection with $R^1$.

It should be appreciated that the exact structure of R is unimportant insofar as completion of the reaction is concerned since the group does not appear in the final compound. On the basis primarily of cost, R preferably is hydroxy, alkyl, alkoxy, aralkyl, or aralkoxy and most preferably hydroxy. In this last regard, it is possible to form a compound of Formula I in situ, that is, in the reaction vessel of the hydrogenation, simply through treatment of N-pyruvyl-L-proline with hydroxylamine thereby forming the hydroxyimine (or oxime), as discussed in greater detail below. Moreover, a chiral R group such as (S)-(−)-α-phenethyl or (S)-(−)-1-(naphth-1-yl)ethyl, can be used.

The metal hydrogenolysis catalyst include known materials and typically are metals of Group 8 such as nickel, palladium, rhenium, platinum, or rhodium. Preparations such as Raney nickel or palladium hydroxide can be employed and the catalyst can be supported on carrier such as carbon or alumina.

In order to achieve the desired stereoselectivity, the hydrogenation is carried out under strongly acidic conditions; i.e., at a pH of less than about 4.

The reaction can be conducted in the presence or absence of an organic solvent. When employed, the solvent can be any inert organic liquid in which the reactant is soluble and which is substantially inert to hydrogenation, as for example lower alkanols, alkanoic acids, alkanes and the like.

The compounds of Formula I are readily prepared through treatment of N-pyruvyl-L-proline with an amine of the formula $H_2N-R$. Optionally, but not necessarily, the reaction can be conducted under conditions which remove water, as for example through use of a Dean-Stark apparatus or by addition of molecular sieves. Typical amines include aminodiphenylmethane, naphth-1-ylmethylamine, benzylamine, hydroxylamine, S-(−)-α-phenethylamine, S-(−)-1-(1-naphthyl)ethylamine, and the like.

Conveniently, the treatment of N-pyruvyl-L-proline with an amine to form a compound of Formula I and the stereo-selective hydrogenation to L-alanyl-L-proline can be conducted in the same reaction vessel, thereby minimizing equipment and potential transfer loss. In fact, the entire reaction sequence described herein, from L-proline and a 2-X-2-Y-propionyl halide to L-alanyl-L-proline, can be conducted without the need to isolate or purify any of the intermediate products.

N-pyruvyl-L-proline can be prepared through any of the known techniques. The present invention, however, also provides an improved process for the preparation of N-pyruvyl-L-proline (including carboxy protected N-pyruvyl-L-proline derivatives) in which a compound of the formula:

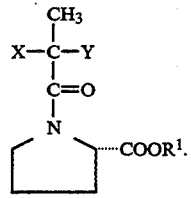
II where X and Y are chloro, bromo, iodo, or together alkylidenedioxy and $R^1$ is hydrogen or a hydrogenolytically removable carboxy protecting group, is hydrolyzed at a pH range of from about 6.5 to about 8.5, preferably at a pH of from about 7 to about 8. This pH range can be controlled through continued addition of base or acid as required or, more conveniently, through use of a buffer. Thus a compound of Formula II can simply be heated in an aqueous media to afford the desired N-pyruvyl-L-proline. Preferably, $R^1$ is hydrogen and X and Y are chloro.

A compound of Formula II can be readily prepared by allowing L-proline and the corresponding 2-X-2-Y-propionyl halide to react in the presence of sufficient aqueous base to provide a pH of at least 9. Preferably the reaction is conducted in an inert organic solvent and ideally, there is sufficient aqueous base present to provide a pH of at least 11.

Thus the present invention permits stereoselective preparation of L-alanyl-L-proline through a four-step process in which (i) L-proline and a 2-X-2-Y-propionyl halide are allowed to react at a pH of at least 9 to produce an N-(2-X-2-Y-propionyl)-L-proline, (ii) this L-proline compound is hydrolyzed at a pH range of from about 6.5 to about 8.5 to yield N-pyruvyl-L-proline, (iii) N-pyruvyl-L-proline is treated with an amine to yield a compound of Formula I, and (iv) the latter is hydrogenated to yield L-alanyl-L-proline in high stereospecificity.

The following examples will serve to further typify the nature of the invention but should not be construed as a limitation on the scope thereof which is defined solely by the appended claims.

In the following examples, the ratio of L-alanyl-L-proline to D-alanyl-L-proline was determined by HPLC using a Waters 510 HPLC pump, Waters 712 WISP, Waters RCM 8×10 Novopak column, Waters 486 Tunable Absorbance Detector, and Shimadzu CR601 Chromatopac Recorder. A mixture of 19 parts of 0.15% aqueous phosphoric acid containing 10 mM octanesulfonic to one part isopropanol can be used as eluant. The flow rate was 1.5 mL/minute with detection at 210 nm. The retention time of L-alanyl-L-proline is 22 minutes, that of D-alanyl-L-proline is 26 minutes. Gas chromatography employed a Supelco SPB-1 Column running at 75° C. for 10 minutes, then 20° C. per minute, then 170° C. for 5 minutes.

EXAMPLE 1

A. L-alanyl-L-proline

To a dry 5 mL flask was added N-pyruvyl-L-proline (0.085 g., 0.46 mmoles, 1.0 eq.), naphth-1-ylmethylamine (0.144 g., 0.92 mmoles, 2.0 eq.), and 2.0 mL absolute ethanol. After 3.0 hours at 25° C., the reaction mixture and 100 mL of ethanol were transferred under nitrogen to a 500 mL Parr shaker flask previously flushed with nitrogen. Palladium-on-carbon (0.02 g., 0.18 mmoles, 0.4 eq.) was added together with 50 mL absolute ethanol. Nitrogen was bubbled through the suspension for 5 minutes and the mixture then hydrogenated at 50 psi for 22 hours using three alternating vacuum/hydrogen gas cycles. The reaction mixture was filtered through Celite ® and concentrated to a yellow oil which was analyzed by HPLC to show an 88% conversion (yield) and a 31% diastereomeric excess of L-alanyl-L-proline. Unreacted imine is the other major peak (5%).

The N-pyruvyl-L-proline utilized as starting material can be conveniently obtained from 2,2-dichloropropionic acid according to the following procedure.

B. 2,2-Dichloropropionyl Chloride

To a dry 100 mL 3-necked flask under nitrogen were added 2,2-dichloropropionic acid (50 g., 0.35 moles, 1 eq.) and dimethylformamide (4 mL, 0.05 moles, 0.15 eq.). Thionyl chloride (35 mL, 0.49 moles, 1.4 eq.) then was added dropwise over 30 minutes. The reaction mixture was warmed to 55° C. for two hours while being following by gas chromatography with methanol quench to insure disappearance of dichloropropionic acid (retention time 8.5 minutes). 2,2-dichloropropionyl chloride was distilled at 120°–121° C. to give 51.7 g. (92% yield) of a slightly yellow oil.

C. N-(2,2-Dichloropropionyl)proline

To a dry 250 mL 3-necked flask were added L-proline (27 g., 0.235 moles, 1.0 eq.) and 100 mL of 6N sodium hydroxide. The solution (pH=14) was cooled to below 10° C. in an ice bath. A solution of dichloropropionylchloride (51.7 g., 0.32 moles, 1.37 eq.) in 40 mL of methylene chloride then was added over 60 minutes keeping the solution temperature below 10° C. (pH=11 after addition). The remaining 2,2-dichloropropionylchloride was rinsed in with an additional 20 mL of methylene chloride and the reaction mixture then warmed to at least 22° C. and stirred for 60 minutes, then the reaction mixture were transferred to a 1 L flask with an additional 200 mL of water as a rinse. The methylene chloride was removed by evaporation and the pH adjusted to 2. Upon cooling to 0° C. for 40 minutes, the solid which forms was collected by filtration using cold water as a rinse to yield N-(2,2-dichloropropionyl)proline which was dried under vacuum (0.1 Torr) for 15 hours to give 44.3 g. (78% yield) which can be further purified through recrystallization from ethyl acetate or ethyl acetate:hexane. m.p. 61°–62° C.

Elemental Analysis: ($C_8H_{11}NO_3Cl_2$); Calculated: C 39.99, H 4.62, N 5.83, Cl 29.58; Found: C 39.98, H 4.59, N 5.78, Cl 29.43.

$^1$H NMR (CDCl$_3$, δ): 6.40 (br s, 2H, $\frac{1}{2}$H$_2$O, COOH), 4.49 (dd, 1H, J=5.0, 8.4 Hz, HCCOO), 4.17–4.03 (m, 2H, CH$_2$ pro), 2.30 (80%), 2.24 (20%) (s, 3H, Me), 2.15–1.96 (m, 4H, CH$_2$ pro).

$^1$H NMR (CD$_3$OD, δ): 4.43 (dd, 1H, J=5.1, 8.8 Hz, HCCOO), 4.23–4.13 (m, 1H, CH$_2$ pro), 4.09–3.98 (m, 1H, CH$_2$ pro), 2.26 (s, 3H, Me), 2.13–1.90 (m, 4H, CH$_2$ pro).

$^{13}$C NMR (CDCl$_3$, δ): 176.2, 164.4, 80.5, 61.4, 49.5, 35.4, 28.3, 25.7.

D. N-pyruvyl-L-proline

To a dry 500 mL 3-necked flask were added dichloropropionylproline (8.9 g., 37.0 mmoles), 125 mL of 0.7M phosphate buffer (pH=7.4) and 50 mL of water. The reaction mixture was heated to reflux with stirring, maintaining the pH at 7.4±0.1, for 18 hours. HPLC indicated 90% N-pyruvyl-L-proline (retention time 3.5 minutes) and 0.4% N-(2,2-dichloropropionyl)-proline (retention time 8.3 minutes).

The pH was adjusted to 3 and the mixture was extracted six times with 150 mL ethyl acetate. The combined organic layers were dried over magnesium sulfate, filtered, and concentrated to yield a yellow oil (4.85 g., 71%) which was dissolved in 100 mL of ethyl acetate, treated with charcoal, filtered through Celite®  and concentrated. Ethyl acetate (200 mL) was added and the mixture concentrated seven to ten times. Crystallization was obtained by cooling with ethyl acetate to give 4.0 g. (58% yield) of white solid N-pyruvyl-L-proline, m.p. 88–89° C.

Elemental Analysis: ($C_8H_{11}NO_4$); Calculated C 51.88, H 6.00, N 7.56; Found: C 51.61, H 6.06, N 7.37.

$^1$H NMR (CDCl$_3$, δ): 5.21 (br s, 3H, H$_2$O, COOH), 4.90 (dd, 1H, J=5.1, 7.8 Hz, HCCOO), 3.85–3.57 (m, 2H, CH$_2$ pro), 2.47 (60%, s, 3H, Me), 2.43 (40%, s, 3H, Me), 2.32–1.89 (m, 4H, CH$_2$ pro).

$^{13}$C NMR (CDCl$_3$, δ): 198.0 (45%), 197.2 (55%), 176.2 (55%), 175.4 (45%), 162.5 (51%), 162.3 (49%), 59.6 (55%), 59.5 (45%), 49.2 (40%), 47.6 (60%), 31.4 (65%), 28.3 (35%), 27.0 (45%), 26.5 (55%), 25.1 (40%.), 21.9 (60%).

When instead 2 mL of acetic acid were added prior to reduction with hydrogen over palladium-on-carbon in the above example, a 45% diastereomeric excess of L-alanyl-L-proline was obtained.

By substituting D-proline for L-proline in the above example, a 70% diastereomeric excess mixture of D-alanyl-D-proline and L-alanyl-D-proline was obtained.

EXAMPLE 2

By substituting 0.168 g. (0.92 mmoles, 2.0 eq.) of aminodiphenylmethane for naphth-1-ylmethylamine in the procedure of Example 1, Part A, a 30% diastereomeric excess of L-alanyl-L-proline was obtained.

EXAMPLE 3

To a dry 5 mL flask was added N-pyruvyl-L-proline (0.085 g., 0.46 mmoles, 1.0 eq.), benzylamine (0.098 g., 0.9 mmoles, 2.0 eq.), and 2.0 mL absolute ethanol. After 3.0 h. at 25° C., the reaction mixture and 100 mL of ethanol were transferred under nitrogen to a 500 mL Parr shaker flask previously been flushed with nitrogen. Palladium hydroxide (0.02 g., 0.18 mmoles, 0.4 eq.) was added together with acetic acid (0.5 mL, 8.7 mmoles, 19 eq.). Nitrogen was bubbled through the suspension for 5 minutes and the mixture then hydrogenated at 50 psi for 24 hours using three alternating vacuum/hydrogen gas cycles. The reaction mixture was filtered through Celite®  and concentrated to a yellow oil which when analyzed. (HPLC) demonstrated a 52% diastereomeric excess of L-alanyl-L-proline.

EXAMPLE 4

N-pyruvyl-L-proline (0.085 g., 0.46 mmoles, 1.0 eq.), hydroxylamine hydrochloride (0.048 g., 0.69 mmoles, 1.5 eq.), sodium acetate (0.056 g., 0.69 mmoles, 1.5 eq.), and 2 mL water and 10 mL ethanol were added to a 25 mL flask. The suspension was heated to reflux for 2 h. The imine was transferred under nitrogen gas with 100 mL ethanol to a 250 mL Parr flask. Palladium hydroxide-on-carbon (0.02 g., 0.18 mmoles, 0.4 eq.) and hydrochloric acid (6 mL, 0.2 moles, 430 eq.) were added and nitrogen was bubbled through for 3 minutes (pH=0.1). The material was hydrogenated for 17 hours as described in Example 1, Part A, to produce a >99.5% diastereomeric excess of L-alanyl-L-proline. Isolation of the product from the reaction mixture can be accomplished by filtering the latter through Celite® , adjusting the pH to 4, and concentrating the resultant solution to one-half volume. The solid which forms is collected by filtration, and held under vacuum to remove any residue solvent.

When the reaction of this example was conducted in the absence of water, a >99.5% diastereomeric excess of L-alanyl-L-proline was obtained.

When conducted in the presence of acetic acid (2 mL, 35 mmoles, 76 eq.) so that the pH was 2.8, a 71% diastereomeric excess of L-alanyl-L-proline was obtained.

When conducted in the absence of acid, pH=4.65, a 33% diastereomeric excess of L-alanyl-L-proline was obtained.

EXAMPLE 5

By following the procedure described in Example 4 but utilizing the following hydrogenolysis catalysts, the indicated diastereomeric excesses of L-alanyl-L-proline were obtained:

| Hydrogenolysis Catalysts | Diastereomeric Excess |
| --- | --- |
| Raney nickel/acetic acid | 32% |
| rhenium-on-carbon | >99.5% |
| palladium-on-carbon | >99.5% |
| platinum-on-carbon | >99.5% |
| rhodium-on-carbon | >99.5% |
| rhodium-on-alumina | 47% |

EXAMPLE 6

To a dry 5 mL flask was added N-pyruvyl-L-proline (0.085 g., 0.46 mmoles, 1.0 eq.), S-(−)-α-phenethylamine (0,110 g., 0.91 mmoles, 2.0 eq.), and 0.5 mL absolute ethanol. After stirring for 3.25 hours at 25° C., the reaction mixture was transferred under nitrogen to a 250 mL Parr shaker flask which previously had been flushed with nitrogen. Raney nickel (0.01 g., 0.17 mmoles, 0.4 eq.) in water was washed with absolute ethanol three times on a Buchner funnel under vacuum and added to the Parr flask with 50 mL absolute ethanol. Nitrogen was bubbled through the suspension for 5 minutes and acetic acid (0.5 mL, 8.7 mmoles, 19 eq.) was added. Nitrogen was bubbled for an additional 2 minutes. The material was hydrogenated at 50 psi (with three alternating vacuum/hydrogen gas cycles) for 16.5 hours and then filtered through Celite® into a fresh 500 mL Parr flask, washing with 200 mL absolute ethanol. After bubbling nitrogen through the mixture, palladium hydroxide-on-carbon (0.02 g., 0.18 mmoles, 0.4 eq.) was added and the mixture then hydrogenated for 5.25 hours at 50 psi (after three evacuation/hydrogen gas at 50 psi cycles). The reaction mixture was filtered through Celite® and concentrated to a yellow oil. HPLC determination of a solution in absolute ethanol established a 94% diastereomeric excess of L-alanyl-L-proline.

EXAMPLE 7

By following the procedure of Example 6 but using S-(−)-1-(naphth-1-yl)ethylamine (0,157 g., 0.91 mmoles, 2.0 eq.) in place of S-(−)-α-phenethylamine and heating the initial reaction mixture 3 hours while conducting the reductions for 16 hours with Raney Nickel and 21 hours for palladium hydroxide-on-carbon, a diastereomeric excess of 99% was obtained for L-alanyl-L-proline as shown by HPLC.

By following the procedure described in the above example but using R-(+)-1-(naphth-1-yl)ethylamine in place of S-(−)-1-(naphth-1-yl)ethylamine to make the imine of N-pyruvyl-L-proline, a 34% diastereomeric excess of L-alanyl-L-proline was obtained.

EXAMPLE 8

By following the procedure described in Example 4 but using the benzyl ester of N-pyruvyl-L-proline (0.4 g, 1.45 mmoles, 1.0 eq.), a 71% diastereomeric excess of L-alanyl-L-proline was obtained.

Additionally, by following the procedure described in Example 4 but using either O-methoxyhydroxyl or O-benzylhydroxyl amine to synthesize the methoxyl or benzoxylamine of N-pyruvyl-L-proline, a 75% or 47% diastereomeric excess of L-alanyl-L-proline was obtained, respectively.

Moreover, by following the procedure described in Example 4 but using ammonium acetate to make the acetylimine of N-pyruvyl-L-proline, a 65% diastereomeric excess of L-alanyl-L-proline was obtained.

EXAMPLE 9

To 2,2-dichloropropionic acid (200 g., 1.4 moles, 1.4 equiv.) and dimethylformamide (16 mL) was added, dropwise over 20 minutes, 147 mL of thionyl chloride. The reaction mixture then was warmed to 75° C. for two hours and monitored by gas chromatography with methanol quench until disappearance of dichloropropionic acid (retention time 8.5 min.), to yield dichloropropionyl chloride as a slightly yellow oil.

EXAMPLE 10

To a dry reaction vessel were added L-proline (115 g., 1.0 moles, 1.0 eq.), 144 mL of 6 N sodium hydroxide and 20 g. solid sodium hydroxide. The clear, colorless solution (pH=11.5) was cooled to +10° C. in an ice bath with stirring. All of the above 2,2-dichloropropionyl chloride was diluted with 50 mL methylene chloride and added to the L-proline solution over 2 hours, keeping the solution temperature below +10 ° C. and the pH at 11.5 by simultaneous addition of 290 mL of 6N sodium hydroxide to yield 2,2-dichloropropionyl-L-proline. The pH was adjusted to 3 by the addition of 216 mL of 6N hydrochloric acid. The solid which formed was collected by filtration using 300 mL of 6N hydrochloric acid as a wash to yield white crystalline 2,2-dichloropropionyl-L-proline which was dried under vacuum (30 Torr) for 18 hours to give 216 g. (90% yield based on L-proline). HPLC at 23 minutes showed ≧96% purity. The recrystallization from ethyl acetate or ethyl acetate-hexane removes 0.5 mole of water but does not significantly improve purity. m.p. 61°–62° C.

Elemental analysis: ($C_8H_{11}NO_3C_{12}$); Calculated: C 39.99, H 4.62, N 5.83, Cl 29.58; Found: C 39.98, H 4.59, N 5.78, Cl 29.43.

$^1$H NMR (CDCl$_3$, δ): 6.40 (br s, 2H, ½H$_2$O, COOH), 4.49 (dd, 1H, J=5.0, 8.4 Hz, HCCOO), 4.17–4.03 (m, 2H, CH$_2$ pro), 2.30 (80%), 2.24 (20%) (s 3H, Me), 2.15–1.96 (m, 4H, CH$_2$ pro).

$^{13}$C NMR (CDCl$_3$, δ): 176.2, 164.4, 80.5, 61.4, 49.5, 35.4, 28.3, 25.7.

EXAMPLE 11

To a dry reaction vessel were added 2,2-dichloropropionyl-L-proline (8.,9 g., 37.0 mmoles) and 125 mL of deionized water. The pH of the mixture was adjusted to 7.2 and heated at reflux with stirring, maintaining the pH at 7.2–7.8, for 16 hours. HPLC indicated 92% pyruvyl-L-proline (retention time 2.8 minutes) and <0.4% 2,2-dichloropropionyl-L-proline (retention time 23 minutes).

The pH was adjusted to 1.5 and pyruvyl-L-proline was extracted from the aqueous solution six times with 150 mL ethyl acetate. The combined organic layers were dried over magnesium sulfate, filtered and concentrated to yield a yellow oil (6.11 g., 89%), which was then dried. Crystallization was obtained with ethyl acetate to give 4.0 g. (58% yield) of white solid pyruvyl-L-proline. m.p. 88°–89° C.

Elemental Analysis: ($C_8H_{11}NO_4$); Calculated: C 51.88, H 6.00, N 7.56; Found: C 51.61, H 6.06, N 7.37.

$^1$H NMR (CDCL$_3$, δ): 5.21 (br s, 3H, H$_2$O, COOH), 4.90 (dd, 1H, J=5.1, 7.8 Hz, HCCOO), 3.85–3.57 (m, 2H, CH$_2$ pro), 2.47 (60%, s, 3H, Me), 2.43 (40%, s, 3H, Me), 2.32–1.89 (m, 4H, CH$_2$ pro).

$^{13}$C NMR (CDCL$_3$, δ): 198.0 (45%), 197.2 (55%), 176.2 (55%), 175.4 (56%),, 162.5 (51%), 162.3 (49%), 59.6 (55%), 59.5 (45%), 49.2 (4.0%), 47.6 (60%), 31.4 (65%), 28.3 (35%), 27.0 (45%), 26.5 (55%), 25.1 (40%), 21.9 (60%).

EXAMPLE 12

To a dry reaction vessel were added 2,2-dichloropropionyl-L-proline (216 g., 0.9 moles, 1.0 equiv.), hydroxylamine hydrochloride (75 g., 1.1 moles, 1.2 equiv.), and 230 mL of 6N sodium hydroxide plus 5 g. solid sodium hydroxide (to achieve a pH of 7.2). The clear yellow solution was heated to reflux at 110° C. with a condenser, with constant stirring and a pH controller to keep the pH at 7.2. The course of reaction was followed by HPLC (about 13 hours). A pH controller was attached to 6M sodium hydroxide and 350 mL of sodium hydroxide was used. HPLC indicated ≦0.6% of 2,2-dichloropropionyl-L-proline (retention time 23 minutes) and 88–92% oxime (retention time 2.8 minutes).

EXAMPLE 13

To a reaction vessel were added 10 g. pyruvyl-L-proline (54 mmole), 5 g. hydroxylamine hydrochloride (72 mmole), 40 mL deionized water, 120 mL ethyl alcohol and 2.9 g. of sodium hydroxide. The reaction mixture was stirred (pH 5.0 after solubilized) and then refluxed for 2.5 hours. The disappearance of starting material can be followed by gas chromatography. After cooling to room temperature, the reaction mixture was transferred to a 2 L Parr shaker flask with 20 mL ethanol as a rinse. To the flask were added 0.45 l of 0.1N hydrochloric acid (the pH of the reaction mixture is 2) and 5 g. of 5% palladium-on-carbon. The reaction mixture was evacuated and purged with three cycles of hydrogen and then hydrogenated at 55 psi with shaking until the reaction was complete as indicated by HPLC.

The reaction mixture was filtered through Celite ® on a Büchner funnel and the pH adjusted to 5.5 with 6N sodium hydroxide. The ethanolic aqueous solution was evacuated on a rotary evaporator keeping the temperature at ≦42° C. Twenty milliliters of ethyl alcohol then were added to the solid. The sodium chloride solids were filtered off using fine filter paper, and the filtrate was cooled to −5° C. and seeded. The white crystalline product was collected (96% d.e.) and washed with 20 mL cold ethanol (≧99% d.e.). The sample was dried under vacuum to give 6.5 g. L-alanyl-L-proline (≧99% chemical purity by HPLC).

HPLC (retention times): 19.9 min. L-alanyl-L-proline and 27.0 min. d-alanyl-L-proline.

T.L.C.: For L-alanine: IPA/water/Acetic acid (70/20/30). No L-alanine observed in sample.

For L-proline: I PA/water/ammonium hydroxide (70/30/20). No L-proline observed in sample.

$^1$H NMR (CD$_3$OD and D$_2$O, δ): 4.4–4.2 (m, 1.4H), 3.94 (q, 0.4H, J=7 Hz), 3.68–3.50 (m, 1.3H), 3.52–3.40 (m, 0.7H), 3.35–3.30 (m, 0.4H), 2.4–2.2 (m, 1.6H), 2.00–1.86 (m, 2.5H), 1.56 (.40%, d, 3H, Me), 1.45 (60%, d, 3H, Me).

$^{13}$C NMR (CD$_3$OD and D$_2$O, δ): 179.5, 179.0, 170.3, 169.3, 63.2, 63.0, 49.2, 49.1, 48.3, 48.2, 32.6, 30.4, 25.7, 23.2, 16.5, 16.1.

What is claimed is:

1. A compound of the formula:

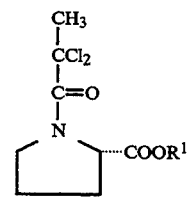

wherein R$^1$ is hydrogen or a hydrogenolytically removable carboxy protecting group.

2. A compound as claimed in claim 1 wherein R$^1$ is a hydrogenolytically removable ester group residue.

3. A compound as claimed in claim 2, wherein said ester group residue is alkyl of 1 to 12 carbon atoms, alkylthio of 1 to 12 carbon atoms, halogeno or aroyl.

4. A compound as claimed in claim 3, wherein said ester group residue is ethyl or methyl.

5. The compound of the formula:

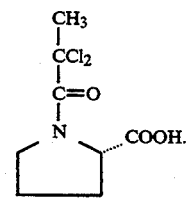

* * * * *